United States Patent [19]

Greenstein

[11] Patent Number: 5,052,393

[45] Date of Patent: Oct. 1, 1991

[54] ULTRASOUND SYSTEM WITH IMPROVED COUPLING FLUID

[75] Inventor: Alan P. Greenstein, Menlo Park, Calif.

[73] Assignee: Hewlett-Packard Company, Palo Alto, Calif.

[21] Appl. No.: 436,097

[22] Filed: Nov. 13, 1989

Related U.S. Application Data

[63] Continuation of Ser. No. 246,126, Sep. 16, 1988, abandoned.

[51] Int. Cl.⁵ .............. A61B 8/00

[52] U.S. Cl. .............. 128/660.01; 128/660.1; 73/644

[58] Field of Search .............. 128/660.01, 660.1, 660.09, 128/660.07, 662.03; 73/644

[56] References Cited

U.S. PATENT DOCUMENTS

| | | | |
|---|---|---|---|
| 4,194,510 | 3/1990 | Proudian | 73/629 X |
| 4,277,367 | 7/1981 | Madsen et al. | 128/660.01 X |
| 4,653,504 | 3/1987 | Kondo et al. | 128/662.03 |
| 4,722,346 | 2/1988 | Chen | 128/662.03 |

FOREIGN PATENT DOCUMENTS

| | | |
|---|---|---|
| AO174167 | 12/1986 | European Pat. Off. . |
| 2149916 | 6/1985 | United Kingdom . |

OTHER PUBLICATIONS

Guildford, GB; "Medical Ultrasound Scanning Couplants", p. 54, Col. 2, lines 1-5, Ultrasonics, vol. 18, No. 2, Mar. 1980.

Hitachi K.K., Patent Abstracts of Japan, vol. 7, No. 182, p. 1327, Aug. 11, 1983.

*Primary Examiner*—Francis Jaworski

[57] ABSTRACT

An ultrasound system, employable for medical imaging, includes an electronics module and a probe. The probe includes a body, a transducer, a driver, a window and coupling fluid. The electronics module includes a transmitter which generates transmission pulses which are converted by the transducer to ultrasound pulses and a receiver which analyzes electrical signals resulting from the conversion of ultrasonic reflections received by the transducer. The electronics module controls delays in the transmission and reception between individual elements of the annular phased array transducer to control focussing. The driver provides for mechanical steering of the transducer. The coupling fluid provides for ultrasonic coupling between the transducer and the window and the subject while permitting the steering movement of the transducer. The coupling fluid is a mixture of 1-Butanol in Glycerol. The attenuation of that mixture can be adjusted without impairing velocity matching by adding suitable amounts of 2-Hydroxyethyl ether.

10 Claims, 3 Drawing Sheets

ULTRASOUND SYSTEM WITH IMPROVED COUPLING FLUID

CROSS REFERENCE TO RELATED APPLICATION

This application is a continuation of application Ser. No. 07/246,126, filed Sept. 16, 1988, now abandoned.

BACKGROUND OF THE INVENTION

The present invention relates to ultrasound and, more particularly, to a system and method providing for improved coupling ultrasound between a transducer and a window of an ultrasound probe.

Ultrasonic imaging is widely used to analyze the internal structure of organisms. For example, ultrasound is often employed to characterize the status of a fetus in a pregnant woman. Ultrasonic imaging is based on the detection of reflections of ultrasonic waves at boundaries characterized by unequal impedances. Such boundaries can represent bones, organ boundaries, changes in tissue type, etc.

Typically, ultrasonic imaging is performed using an ultrasonic probe electrically coupled to an electronics module. The probe generally comprises a body serving as a handle, a cap or window which can pressed against the skin of a subject being imaged, and a electro-acoustic transducer enclosed by the body and window. The electronics module generates electrical pulses to be converted to ultrasonic pulses that are propagated through the window and into the subject.

A single ultrasonic pulse can result in multiple reflections due to multiple impedance boundaries along its path of propagation. As these reflections are detected by the probe, they are converted by the transducer to an electrical signal which represents depth by time and impedance mismatches by amplitude. The electronics module analyzes this signal to recover the imaging information which can then be displayed and/or recorded as desired.

The quality of the image obtained is largely dependent on the sensitivity with which the probe can detect reflections. A substantial portion of the energy of an ultrasonic pulse is absorbed by the probe or the body. The remaining energy is distributed among multiple reflections. Only a small fraction of each reflection is directed toward the probe, and much of that small fraction is absorbed before reaching the transducer. The transducer must be able to detect the occurrences and amplitude of these reflections, despite the small amounts of energy in each reflection.

Sensitivity is a function of the aperture, or energy-gathering area, of the transducer. A transducer with a large aperture can receive a greater portion of reflected acoustic energy. On the other hand, a larger aperture implies a shallower depth of focus. A transducer is shaped and/or operated so that there is, at any given time, a single depth at which the transducer's ability to resolve depth is at a maximum. In practice, maximal resolution is not necessary, but some threshold resolution below this maximum can be required by many imaging applications. When a transducer with a small aperture is used, the range of depths for which a given threshold is met or exceeded is larger than the corresponding range of depths available when a large aperture is used.

When the range of depths of interest is greater than the depth of field of a probe, it is necessary to obtain imaging information using focal points at successive depths. Finer steps between focal points are required for a larger aperture. Herein, the process of changing the focal length of a probe during image gathering is referred to as "zooming".

Zooming permits high resolution imaging along a single trajectory. To obtain a two-dimensional image of a "slice" of a subject, the direction of ultrasound propagation must be panned, i.e., swept transversely or "steered". It is this steering action that gives many ultrasound images their fan-shaped form. Herein, steering and zooming are collectively referred to as "scanning".

Scanning is performed differently by various probe types. A small aperture probe with a spherical transducer can rely on a fixed focus and mechanical steering for imaging. Theoretically, a single element transducer could be mechanically deformed to provide for zooming and, thus, larger apertures. However, annular array transducers have been developed in which time delays between concentric elements provide the zooming function; annular array transducers generally employ mechanical steering. Just as phased-arrays are used in radar, it is possible to implement a rectangular array ultrasound transducer in which all scanning is performed electronically. Such rectangular arrays involve considerable processing complexity and are not widely used. Linear phased arrays are simpler to implement and also permit electronic zooming and steering; however, elevational resolution (transverse to depth and pan) is poor.

While each probe design has its advantages, the annular array stands out for allowing high resolution imaging in all directions while demanding less in the way of processing to generate an image from the received reflections. Zooming can be performed electronically at very high speeds for each mechanically controlled pan position.

One challenge in designing large aperture, mechanically scanned ultrasonic transducers such as an annular array transducers is to couple ultrasound transmissions between the probe and the subject optimally. For obvious reasons, including subject comfort, the moving transducer cannot be in intimate contact with the subject. Instead, intimate contact with the subject is made by the probe window. The window material is selected to be safe, comfortable, rigid and transmissive of ultrasonic energy. A more subtle criterion is the requirement that the acoustic refractive index at ultrasound frequencies be closely matched to the subject being imaged. In other words, the acoustic velocities of window and subject should be matched. The purpose of this matching is to minimize image distortion due to changes in beam direction at the subject-window boundary.

In addition, it is desirable to match the ultrasonic impedance of the window to the subject to minimize reflections at that surface. Such reflections bear no useful information, create reflections internal to the probe which can interfere with image clarity, and dissipate energy which could otherwise contribute to useful reflections. However, some compromise in impedance matching is tolerated to accommodate other criteria, particularly rigidity of the window.

A fluid medium is typically interposed between a mechanically panned transducer and the associated probe window to permit steering motion while providing appropriate ultrasonic coupling between the transducer and the window and subject. The requirements for coupling include matching of transmission velocity and impedance among the fluid, window and subject for the same reasons discussed above with respect to matching the window to the body. In addition, the attenuation of the fluid must be considered to balance the requirement of efficient transmission of ultrasound and the need to damp reflections internal to the probe which could create image artifacts and otherwise degrade image quality.

These requirements generally constrain selection of the medium material to be a liquid sealed in a chamber defined by the probe body and window. It is difficult to determine the range of coupling fluids used in mechanically scanned probes, since many of these are proprietary. Various organic liquids have been tried. Frequently, materials are mixed in an attempt to combine the characteristics of each component. However, such most combinations interact in a non-linear manner, rendering the outcome of a mixture unpredictable. While tables of attenuation and impedance are available, selection of a coupling fluid is generally a matter of trial and error.

One problem with known coupling fluids is that it is difficult to vary one parameter of interest, e.g., impedance, without affecting another, e.g., velocity. Often, it is not possible to "tweak" a fluid mixture to obtain the desired properties. Moreover, these properties must be maintained within acceptable tolerances over a range of operating tempertures, further excluding otherwise acceptable coupling fluids.

A number of different materials, e.g., silicone-based oils or mixtures of Glycerol with Propylene Glycol, have been successfully employed as coupling fluids for small aperture probes. However, images produced by larger aperture probes using the same fluids have been plagued by artifacts apparently due to internal reflections. What is needed is an ultrasound system and method for producing clearer images when using large aperture probes. Preferably, such a system and method would employ a coupling fluid for which one parameter of interest can be adjusted without significantly changing another parameter.

SUMMARY OF THE INVENTION

The present invention is based on a probe design method which, rather than maximizing its transmissivity, optimizes the attenuation of the coupling fluid within a range selected to render the amplitudes of internal reflections insignificant by the time reflections of interest return to the probe transducer. The coupling fluid between the transducer and a probe window includes a mixture of 1-Butanol and Glycerol. Attenuation can be adjusted downwardly by including a suitable amount of 2-Hydroxyethyl Ether with the mixture. The invention is used to its best advantage in a mechanically scanned probe with a large aperture transducer. However, it is also applicable to other ultrasonic probes employing a coupling fluid.

The importance of attenuation of the coupling fluid is most critical in large aperture probes. In a small aperture probe, the distance between the transducer and the window and the length of the mean free path of ultrasound, i.e., acoustic energy having a frequency of about 20 kilohertz (kHz) or greater, through the medium are both relatively short. This results in relatively many reflections per unit time. Each reflection is accompanied by some attenuation and some dissipation or loss due to transmission; reflections off the transducer are particularly attenuative. By the time a reflection of interest arrives at the transducer, a sufficient number of internal reflections occur to reduce the energy of the internal reflections to an acceptable level.

In a large aperture probe, the mean free path is longer and there are fewer reflections per unit time. In other words, the coupling fluid in a large aperture probe serves a relatively more important role in attenuating internal reflections. For this reason, the present invention provides for a more attenuative coupling fluid than is typically employed in ultrasound probes.

More importantly, the present invention provides for more precise control over the attenuation of the coupling fluid. Since the coupling fluid in a large aperture probe is a relatively important factor in attenuating internal reflections, it follows that performance of the incorporating ultrasound system is more sensitively affected by the extent of attenuation imposed by the coupling fluid. For this reason, it is important that the attenuation be precisely established at an optimum level.

It is challenging to determine this optimum level. This optimum level varies in as yet difficult to predict ways on probe composition and geometry. Furthermore, for given probe, this optimum can vary according to the depths of interests and the types of tissue or other materials being explored. Therefore, coupling fluids are usually selected through a process of trial and error.

This trial and error process can be quite tedious. In generally, adjustments to a fluid mixture to change attenuation also change velocity and/or impedance, which must be kept within predetermined bounds. Generally, fluid characteristics do not combine linearly so that it is difficult to predict the values of a mixture without testing it. Thus, a mixture which is suitable for a particular probe and application might not be modifiable for a slightly different probe or application.

The present invention addresses this problem in a probe which includes a coupling fluid the attenuation of which can be precisely adjusted without impairing velocity and impedance matching. The preferred ratio of 1-Butanol in Glycerol provides a relatively attenuative fluid. Lower attenuations are attainable by adding 2-Hydroxyethyl Ether. Small changes in velocity and impedance can be compensated by adjusting the ratio of 1-Butanol in Glycerol slightly.

The present invention provides for an economical and high performance ultrasound system. The economy results from the greatly reduced design time required to find an appropriate coupling fluid to achieve different attenuations. The fluid components are known as are the proportions required to attain specific levels of attenuation. This greatly relieves the amount of experimentation required to achieve optimal probe performance. Probe performance is enhanced because larger aperture probes are made more practical and because attenuation can be more closely matched to probe characteristics and to applications. These and other features and advantages are apparent from the description below with reference to the following drawings.

DESCRIPTION OF THE PREFERRED EMBODIMENTS

Figure 1:
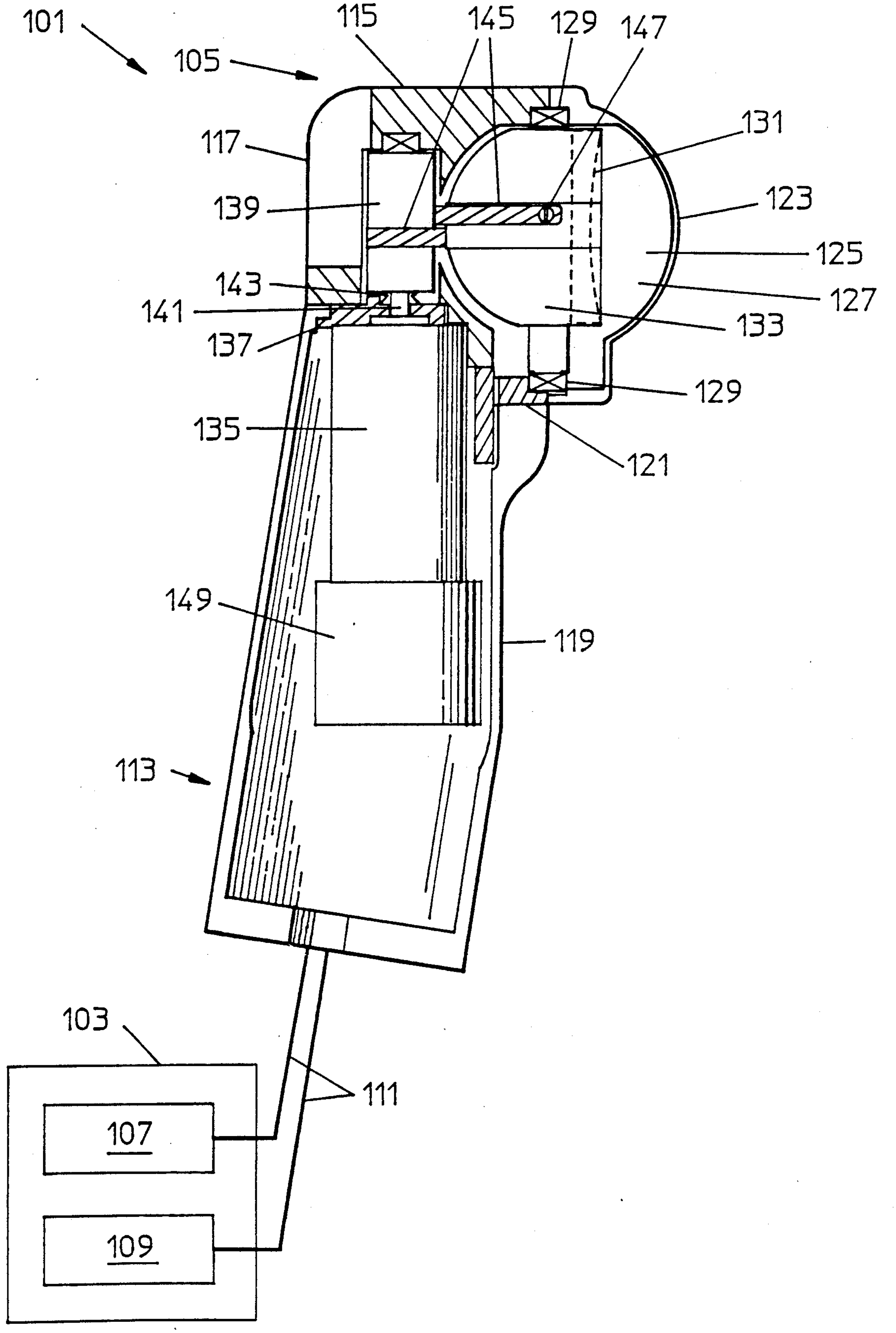
FIG. 1 is a sectional view of a probe in accordance with the present invention.

An ultrasound system 101 includes an electronics module 103 and a probe 105, schematically shown in FIG. 1. Electronics module 103 includes transmitter electronics 107 and receiver electronics 109 coupled via cable 111. Cable 111 includes lines for supplying power and ground potentials to probe 105, for delivering pulses from transmitter electronics 107 to probe 105, for delivering received signals from probe 105 to receiver electronics 109.

A housing 113 for probe 105 includes a probe head 115, a probe back 117 and a probe handle 119. Head 115 is attached to handle 119 via handle bracket 121. A probe window 123 is rigidly attached to head 115. Window 123, head 115 and back 117 collectively define a chamber 125 which is filled with a coupling fluid 127. A transducer 131 is mounted in a spherical frame 133, which is pivotably mounted in head 115 with bearings 129. A motor 135 is mounted in handle 119 by means of a motor mount 137. Motor 135 drives a pinion 139 via a shaft 141. A shaft seal 143 prevents fluid 127 from escaping into handle 119. Drive bands 145 transfer pinion motion to provide for steering of frame 133, and thus transducer 131. Bands 145 are attached to frame 133 with bolts 147, one of two being shown. An optical encoder 149 provides information on pan position to receiver electronics 109 required to construct an ultrasound image.

Ultrasound system 101 is typical of ultrasound systems using annular phased array transducers except for modifications to incorporate the relative large aperture transducer 131 for increased sensitivity and the selection of attenuative coupling fluid 127 to compensate noise problems introduced due to the increased aperture size. The aperture of transducer 127 about three centimeters (cm), compared to a more typical 1.5 cm aperture. Coupling fluid 127 is substantially a two-component mixture consisting primarily of 1-Butanol (Butyl Alcohol) in Glycerol. This two component mixture is characterized by a velocity 1540 m/s, an impedance of 1.7 Mrayls and an attenuation of 4.1 dB/cm at 4.5 MHz. Temperature sensitivity is given by a velocity slope of −2.4 m/s/deg C. and an attenuation slope of −0.1 dB/cm/deg.C.). Both velocity and attenuation decrease with higher percentages of Butanol.

Figure 2:
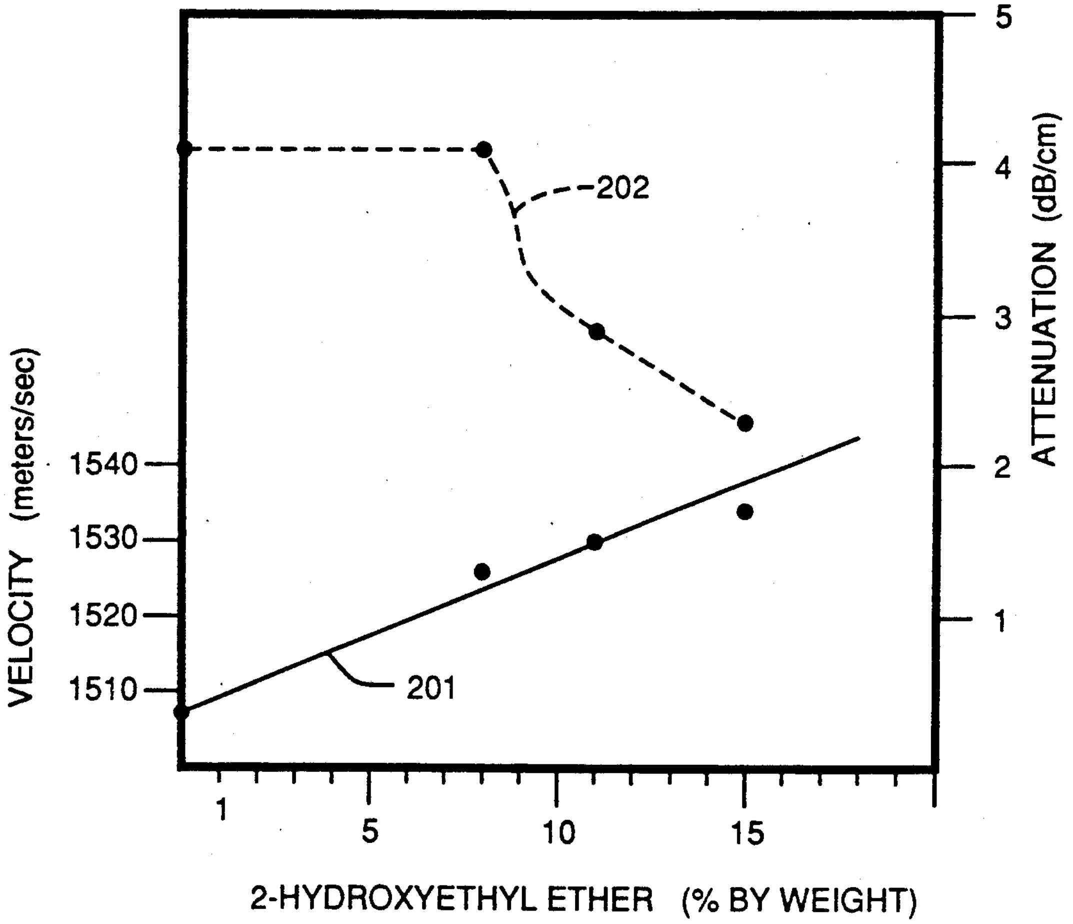
FIG. 2 is a graph indicating the effect on attenuation and velocity of adding 2-Hydroxyethyl Ether to a mixture of 1-Butanol in Glycerol in accordance with the present invention.

In an alternative embodiment of the present invention, 2-Hydroxyethyl Ether is added to the mixture to reduce attenuation. The effects of this addition for an illustrative composition are shown in FIG. 2. The starting point is a 1-Butanol/Glycerol mix at velocity = 1500 m/s, as indicated by line 201, and attenuation = 4.1 dB/cm, as indicated by line 202. With the addition of 8% by weight of 2-Hydroxyethyl Ether, there is insignificant change in attenuation and a small change in velocity to 1526 m/s. With an 11% by weight mixture of the 2-Hydroxyethyl Ether, attenuation drops dramatically to 2.9 dB/cm while velocity increases only slightly to 1530 m/s. With a 15% by weight mixture, attenuation decreases to 2.3 dB/cm while velocity increases to 1534 m/s.

Looked at another way, by decreasing the percentage of 2-Hydroxyethyl Ether in the mixture from 15% to 8%, a 78% increase in attenuation can be attained while velocity decreases only half of a percent. Thus, significant attenuation control is afforded while velocity is maintain within narrow bounds. It should be noted that few fluids possess the desirable quality of allowing one to vary the attenuation without driving the velocity beyond allowable values. For purposes of comparison, changing the ratio of 1-Butanol to Glycerol to attain the same level of attenuation would result in an acceptable velocity of about 1400 m/s.

Figure 3:
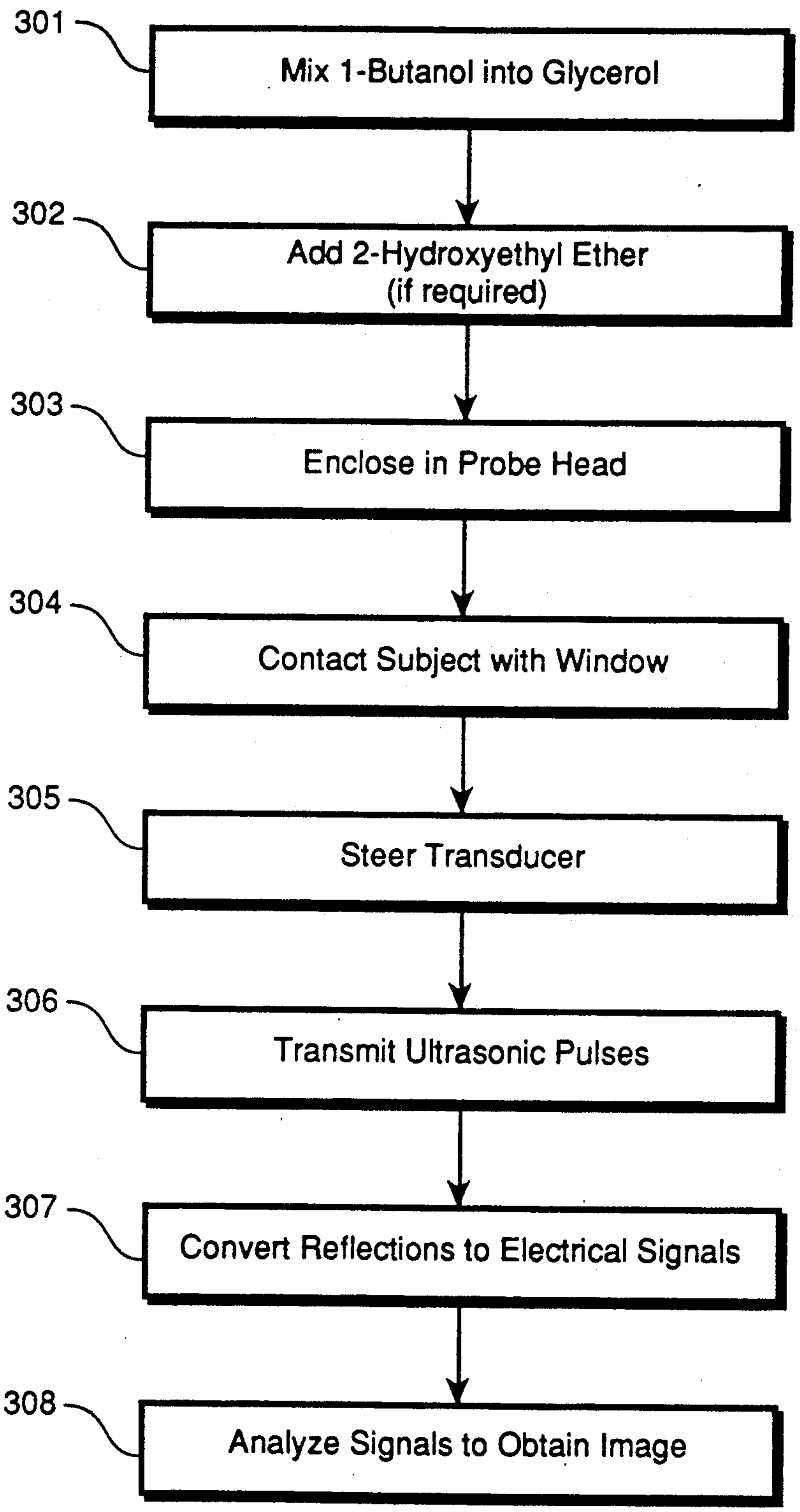
FIG. 3 is a flow chart depicting a method of coupling ultrasonic energy between a mechanically scanned ultrasound generator and an ultrasound window in accordance with the present invention.

FIG. 3 is a flow chart of a method in accordance with the present invention. The first step 301 is mixing 1-Butanol into Glycerol to attain velocity and impedance matched levels. The next step 302 is to add, as necessary, 2-Hydroxyethyl Ether to decrease attenuation to an appropriate level. This fluid is to be enclosed, at step 303, in the head of the ultrasonic probe. The window of the probe is to be pressed, at step 304, against a subject and the transducer of the probe mechanically scanned, at step 305, relative to the subject. Ultrasound pulses are transmitted, at step 306, from the transducer through the fluid, through the window and into the subject. At least some of the ultrasound reflections from the subject are transmitted through the window, the fluid and converted, at step 307, by the transducer to electrical signals. These electrical signals are then analyzed, at step 308, to generate an image characterizing the subject.

The foregoing is a description of the preferred embodiments of the present invention. In addition, different probe dimensions and geometries are accommodated. A variety of transmission and receiver electronics are provided for, including both digital and analog based electronics. Different transducer types and geometries are provided for. The body supporting the transducer can have any of innumerable shapes and characteristics. A variety of enclosure and window types and materials are provided for. The drive system for steering the transducer can assume a variety of configurations. In addition to the components described above, the coupling fluid can include other components which modify, dilute critical characteristics or which leave these characteristics unaffected but serve an ancillary function. Other modifications and variations are provided for by the present invention, the scope of which is limited only by the following claims.

What is claimed is:

1. An apparatus comprising:

transmission electronics for providing electrical pulses;

receiver electronics for interpreting electrical signals;

a transducer for converting electrical pulses to ultrasound energy and ultrasound energy to electrical signals, said transducer being coupled to said transmission electronics for receiving said electrical pulses therefrom, said transducer being coupled to said receiver electronics for providing said electrical signals thereto;

a body supporting said transducer so that the translational position of said transducer can be controlled by moving said body;

enclosure means for enclosing said transducer, said enclosure means being rigidly coupled to said body so as to define a fluid-tight chamber including said transducer, said enclosure means including a window rigidly coupled to said body, said window being substantially transmitting of ultrasonic energy;

drive means for moving said transducer relative to said body so that ultrasound energy radiated by said transducer can be scanned relative to said body; and a fluid enclosed by said chamber, said fluid including a mixture 1-Butanol and Glycerol.

2. The apparatus of claim 1 wherein the ratio of 1-Butanol to Glycerol in said mixture is between 23% and 37%.

3. The apparatus of claim 1 wherein said fluid also includes 2-Hydroxyethyl Ether.

4. A method for characterizing an organism, said method comprising the steps of:

pressing the window of a probe against the organism;

scanning a electro-acoustic transducer within said probe relative to said organism;

transmitting a series of electrical pulses to said transducer so as to generate a series of ultrasonic pulses;

transmitting said ultrasonic pulses through a fluid including a mixture of 1-Butanol and Glycerol, said fluid acoustically coupling said transducer and said window;

transmitting said ultrasonic pulses from said fluid through said window and into said organism so as to produce ultrasonic reflections;

transmitting said ultrasonic reflections from said organism through said window and through said fluid to said transducer to produce electrical signals; and analyzing said signals to characterize said organism.

5. The method of claim 4 wherein the ratio of 1-Butanol to Glycerol in said mixture is between 23% and 37%.

6. The method of claim 4 wherein said fluid also includes 2-Hydroxyethyl Ether.

7. A method of coupling acoustic energy between a mechanically scanned ultrasound generator and an ultrasound window, said method comprising the step of:

filling the space between said generator and said window with a fluid including a mixture of 1-Butanol and Glycerol.

8. The method of claim 7 further comprising the step of preparing said fluid so that the ratio of 1-Butanol to Glycerol in said mixture is between 23% and 37%.

9. The method of claim 7 further comprising the step of preparing said fluid so that it also includes 2-Hydroxyethyl Ether.

10. A method according to claim 7, comprising the step of adding 2-Hydroxyethyl Ether to said mixture to achieve a desired reduction in attenuation of ultrasound by said fluid.

* * * * *